US011083346B1

United States Patent
Krenke (10) Patent No.: US 11,083,346 B1
(45) Date of Patent: Aug. 10, 2021

(54) FREESTANDING AND HIGH-VOLUME CAPACITY DISPENSER FOR DISPENSING A MEASURED AMOUNT OF A LIQUID HAND DISINFECTANT

(71) Applicant: Spencer Wayne Krenke, Key West, FL (US)

(72) Inventor: Spencer Wayne Krenke, Key West, FL (US)

(*) Notice: Subject to any disclaimer, the term of this patent is extended or adjusted under 35 U.S.C. 154(b) by 0 days.

(21) Appl. No.: 17/185,505

(22) Filed: Feb. 25, 2021

Related U.S. Application Data (60) Provisional application No. 63/055,049, filed on Jul. 22, 2020.

(51) Int. Cl.
| *A47K 5/12* | (2006.01) |
| *A61L 2/00* | (2006.01) |
| *A61L 2/26* | (2006.01) |

(52) U.S. Cl.
CPC .......... *A47K 5/1202* (2013.01); *A47K 5/1217* (2013.01); *A61L 2/0088* (2013.01); *A61L 2/26* (2013.01); *A61L 2202/14* (2013.01); *A61L 2202/15* (2013.01)

(58) Field of Classification Search
CPC ........ A61L 2/088; A61L 2/26; A61L 2202/14; A61L 2202/15; A47K 5/1202; A47K 5/1217

See application file for complete search history.

(56) References Cited

U.S. PATENT DOCUMENTS

| 4,769,863 A | * | 9/1988 | Tegg | A47K 1/12 4/616 |
| 2007/0213877 A1 | * | 9/2007 | Hart | G07C 9/22 700/282 |
| 2007/0261162 A1 | * | 11/2007 | Atkinson | E03B 1/04 4/623 |
| 2009/0152293 A1 | * | 6/2009 | Sayers | A47K 5/1205 222/52 |

* cited by examiner

*Primary Examiner* — Sean E Conley
(74) *Attorney, Agent, or Firm* — Barry Choobin; Patent 360

(57) ABSTRACT

A freestanding high-volume capacity liquid hand disinfectant dispensing station that can dispense a measured amount of liquid hand disinfectant over the user's hand. The dispensing station having an upstanding housing that includes a base-section, a mid-section, and a top section. The base-section can contain and conceal the liquid hand disinfectant formulation in a volume capacity ranging from 2-100 Liters. A pump assembly can be coupled to the mid-section which draws the liquid hand disinfectant formulation and dispenses a measured amount through a spout coupled on top of the housing.

17 Claims, 7 Drawing Sheets

FREESTANDING AND HIGH-VOLUME CAPACITY DISPENSER FOR DISPENSING A MEASURED AMOUNT OF A LIQUID HAND DISINFECTANT

CROSS-REFERENCE TO RELATED APPLICATIONS

This application claims the benefit of a U.S. Provisional Patent Application No. 63/055,049 filed on Jul. 22, 2020, entitled "FREESTANDING, HIGH-VOLUME CAPACITY DISPENSER STATION FOR LIQUID HAND DISINFECTANT PREPARATIONS", the entire content of which is incorporated herein by reference.

FIELD OF INVENTION

The present invention relates to a liquid dispenser, and more particularly, the present invention relates to a freestanding portable, and high-volume capacity liquid dispenser that can dispense a small amount of liquid onto the hands.

BACKGROUND

Hands are a key source for the spread of pathogens among humans. Proper hand-hygiene has been scientifically proven to reduce pathogens and prevent illness through the spread of pathogens which exist on the hands. The COVID-19 pandemic in 2020 that engulfed a majority of the population has heightened the importance of hand hygiene. Frequent hand sanitization by washing the hands with soap and water or rubbing a disinfectant on hands is frequently recommended by healthcare professionals. In public places, the dispensers having Liquid hand disinfectant preparations are commonly used to reduce pathogens on the hands when washing with soap and water are not available or washing of the hands in not practical.

Maintaining freestanding liquid hand disinfectant dispensers in public space environments including multi-unit residential buildings, retail environments, commercial, industrial, sports and entertainment venues, transit systems and stations, hospital, healthcare environments, schools, offices, all types of government spaces and the like places where numerous persons in public congregate are beneficial to the public health.

Liquid hand disinfectant dispensers are available that can be mounted to a wall, a stand, or placed on an upstanding structure that is within reach of hands. The known liquid hand disinfectant dispensers, either for commercial, public, or professional use are generally available in volume capacities ranging between 500 mL to 2000 mL. Such dispensers can be refillable with liquid hand disinfectant using the reservoir within the dispenser, or the dispensers may use disposable pre-filled reservoirs which are commercially available to replace the empty reservoirs.

However, refilling the reservoirs of prior art liquid hand disinfectant dispensers can be a laborious task. Also, there could be frequent time gaps when the reservoir remains empty and not available for hand disinfection. Additionally, the prior art lightweight and unstable freestanding dispensers used in high-traffic areas can easily topple creating a hazard with liquid preparation spilling to the floor surface, creating a potential hazard to the public. Additionally, in a high-traffic area, such as an entertainment or sports event, the known dispensers with typical 500 mL to 2000 mL capacity are insufficient in volume capacity to remain full to fulfill user demand before becoming empty and requiring a refill service. As a result, they either remain empty for a duration insufficient to fulfill demand or require too frequent refills at a cost of labor. Both stocking and frequent replacing can increase both the product cost and labor cost.

SUMMARY OF THE INVENTION

The principal object of the present invention is therefore directed to a freestanding and large volume capacity liquid hand disinfectant dispensing station.

It is another object of the present invention that the dispensing station can be used for commercial, public, or professional use.

It is still another object of the present invention that the dispensing station maintains significant and superior volume capacity to meet the specific high-traffic preparation volume requirements.

It is yet another object of the present invention that the dispensing station is of superior footprint and weight making it stable on the ground.

It is an additional object of the present invention that the dispensing station can easily withstand nudges and shocks while being portable and freestanding and not top heavy.

It is a further object of the present invention that the dispensing station may not require frequent replacement of the liquid hand disinfectant contained in the housing of the dispensing station.

It is still a further object of the present invention that a high-volume capacity replacement liquid hand disinfectant can be contained within the dispensing station's interior and is quick and easy to replace.

It is still an additional object of the present invention that the dispensing station is operationally cost-effective and time-saver.

In one aspect, disclosed is a freestanding high-volume capacity liquid hand disinfectant dispensing station that can dispense a small amount of liquid disinfectant for hand sanitization. The dispensing station having upstanding housing including a base-section, a mid-section, and a top section. The base-section can enclose a superior high-volume capacity liquid disinfectant formulation. A pump can be coupled to the mid-section which draws the liquid disinfectant formulation from the liquid disinfectant supply and dispenses a measured dose of the liquid disinfectant formulation to the user's hands through a spout coupled on top of the housing.

BRIEF DESCRIPTION OF THE DRAWINGS

The accompanying figures, which are incorporated herein, form part of the specification and illustrate embodiments of the present invention. Together with the description, the figures further explain the principles of the present invention and to enable a person skilled in the relevant arts to make and use the invention.

DETAILED DESCRIPTION

Subject matter will now be described more fully hereinafter with reference to the accompanying drawings, which form a part hereof, and which show, by way of illustration, specific exemplary embodiments. Subject matter may, however, be embodied in a variety of different forms and, therefore, covered or claimed subject matter is intended to be construed as not being limited to any exemplary embodiments set forth herein; exemplary embodiments are provided merely to be illustrative. Likewise, a reasonably broad scope for claimed or covered subject matter is intended. Among other things, for example, the subject matter may be embodied as methods, devices, components, or systems. The following detailed description is, therefore, not intended to be taken in a limiting sense.

The word "exemplary" is used herein to mean "serving as an example, instance, or illustration." Any embodiment described herein as "exemplary" is not necessarily to be construed as preferred or advantageous over other embodiments. Likewise, the term "embodiments of the present invention" does not require that all embodiments of the invention include the discussed feature, advantage, or mode of operation.

The terminology used herein is for the purpose of describing particular embodiments only and is not intended to be limiting of embodiments of the invention. As used herein, the singular forms "a", "an" and "the" are intended to include the plural forms as well, unless the context clearly indicates otherwise. It will be further understood that the terms "comprise", "comprising,", "includes" and/or "including", when used herein, specify the presence of stated features, integers, steps, operations, elements, and/or components, but do not preclude the presence or addition of one or more other features, integers, steps, operations, elements, components, and/or groups thereof.

The following detailed description includes the best currently contemplated mode or modes of carrying out exemplary embodiments of the invention. The description is not to be taken in a limiting sense but is made merely for the purpose of illustrating the general principles of the invention, since the scope of the invention will be best defined by the allowed claims of any resulting patent.

Disclosed is a freestanding high-volume capacity dispensing station for liquid hand disinfectants that can dispense each time a small amount of the liquid disinfectant for hand sanitization. The dispensing station having a large hollow interior capacity sufficient to contain within a high-volume capacity liquid disinfectant supply which is sufficient to dispense more than 20,000 typical activation volumes of liquid disinfectant of a prescribed amount sufficient to sanitize the hands of an adult human. For example, the disclosed dispensing station can dispense typical activation volumes of the liquid disinfectant formulation in the range of 4,000 to 50,000. Each activation can be typical of a volume from 0.5 ml to 2 ml. The dispensing station is free-standing i.e., supported on the ground without any support of a vertical structure, such as a wall. Despite being freestanding on the ground, the disclosed dispensing station is stable and can easily withstand accidental nudges and shocks. The housing of the dispensing station can be frustoconical shape having the diameter of the bottom 28-45% greater than the diameter of the top for enhanced stability. Disclosed dispensing station has the advantage of both the portable dispensing station and the stability of a fixed dispensing station. The disclosed dispensing station can be used in public places, and places having high traffic. The disclosed dispensing station additionally has an aesthetic outer appearance and could be easily installed. Moreover, the disclosed dispenser deters theft because of its heavier weight and footprint volume and the high-volume capacity liquid disinfectant contained within the interior of the dispensing station.

Figure 1:
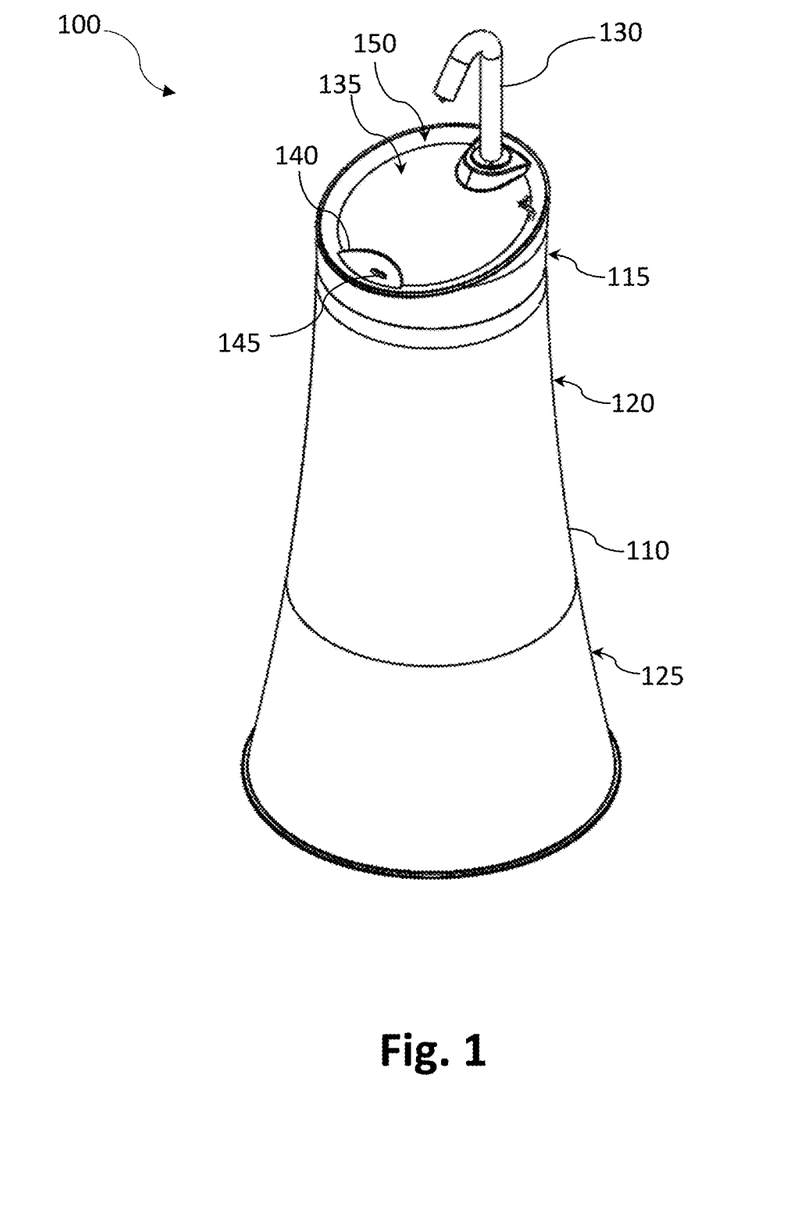
FIG. 1 is a perspective view of the liquid hand disinfectant dispensing station, according to an exemplary embodiment of the present invention.
Figure 2:
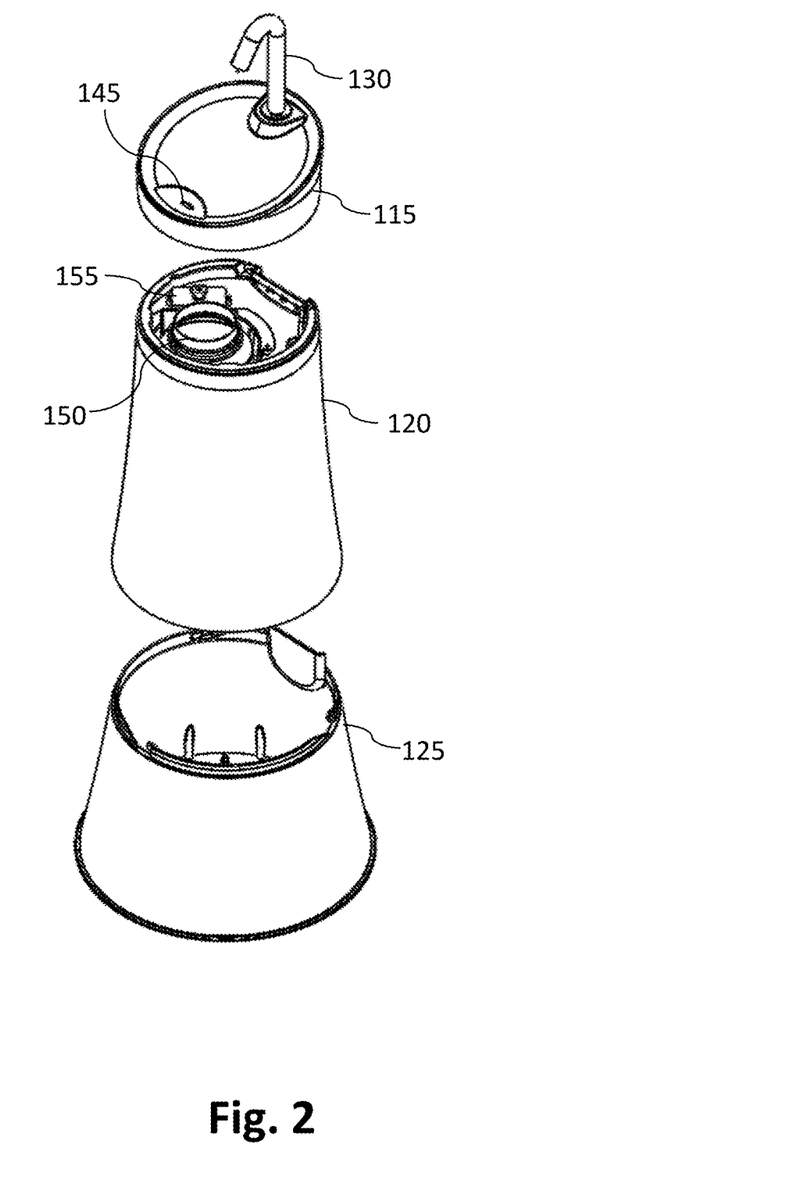
FIG. 2 is an exploded view showing three sections of the housing of the liquid hand disinfectant dispensing station, according to an exemplary embodiment of the present invention.

Now referring to FIG. 1, which shows an exemplary embodiment of the liquid disinfectant dispensing station. The dispensing station 100 having an upstanding housing 110 that is cylindrical having a wider bottom that may resemble a frustoconical geometry. The housing 110 having a top section 115, a mid-section 120, and a bottom section 125. FIG. 2 shows the three sections of the housing 110 separate from each other. The housing 110 is hollow from inside to accommodate the high-volume capacity liquid hand disinfectant formulation and a pumping assembly. FIG. 1 shows the top of the dispensing station 100 having a spout 130 for dispensing the liquid disinfectant on the user's hand. The base of the spout 130 is positioned near the edge of platform 135. The platform 135 is sloped downwards from the spout towards the opposite end, such that excess liquid from the spout or the user's hands which drops on the platform can flow towards the opposite end of the platform. The end of the platform 135 opposite the spout 130 is having a valley 140 which is a depression in the platform 135. The bottom of the valley is having a drain aperture 145, such that the liquid disinfectant which drops on the platform 135 can flow down into the drain aperture 145. The platform is having an upstanding sloped rim 150 surrounding the entirety of the platform.

Referring to FIG. 2, which shows the base-section 125 of the housing which is hollow inside. The base-section 125 is having a flat base plate that can be supported on the floor. The hollow base-section 125 is sufficient to contain a high-volume capacity liquid hand disinfectant. In one case, the hollow interior of base-section 125 and a portion of mid-section 120 above can contain a volume capacity ranging from 2 Liters-25 Liters. Interior volume capacities of up to 100 Liters can also be provided for increased capacity of the dispensing station. The hollow interior is suitable for either disposable liquid hand disinfectants units or refillable using a rigid container suitable for this purpose. In the case of the disposable liquid hand disinfectant unit, both rigid and flexible packaging options can be utilized.

The mid-section 120 of the housing 110 shown in FIG. 2 can have a drain reservoir 150 that is having an opening in fluid communication with the drain aperture 145. Any liquid which flows into the drain aperture 145 can be collected in the drain reservoir 150. Alongside the opening of the drain reservoir 150 can be seen a power unit 155 that may be connected to a battery or another source of power.

Figure 3:
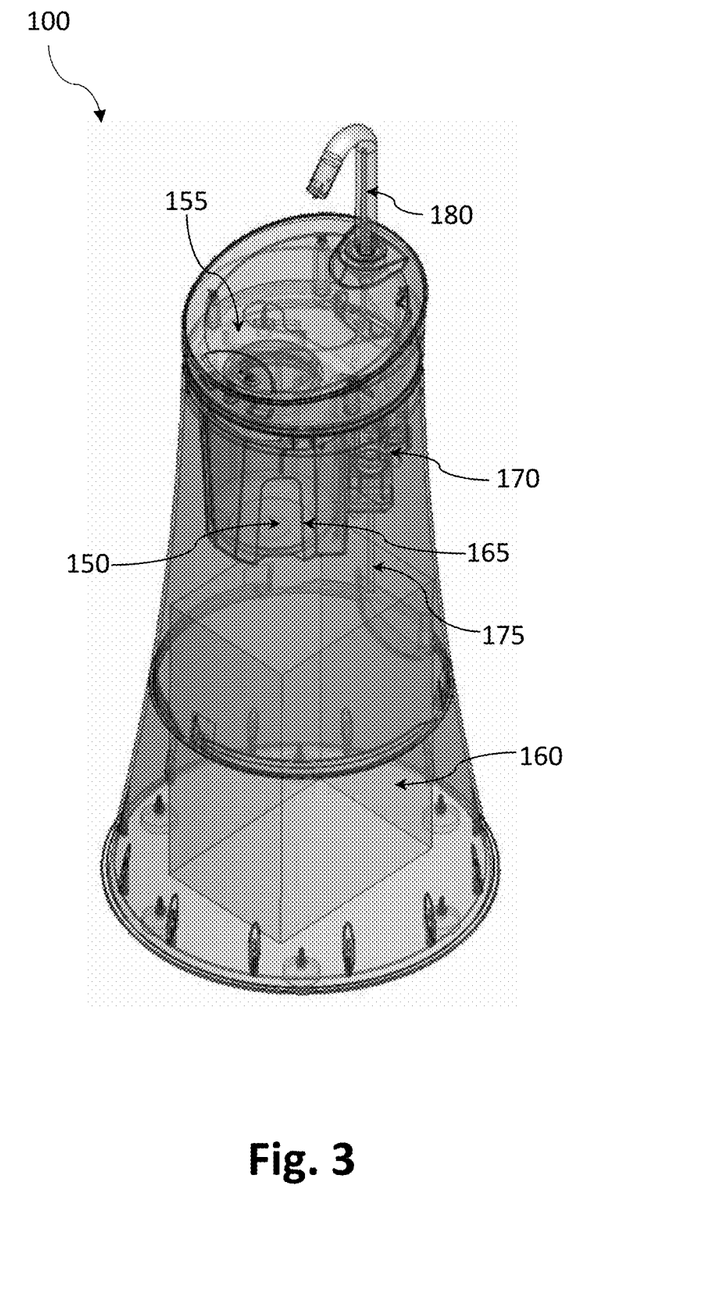
FIG. 3 is the liquid hand disinfectant dispensing station of FIG. 1 with a transparent housing to show the inner components, according to an exemplary embodiment of the present invention.

Referring to FIG. 3 which is a perspective view of the dispensing station 100 having transparent housing 110 for showing the inner components. The housing 110 encloses the high-volume capacity liquid hand disinfectant supply 160 that is contained and concealed inside the base-section 125 of the housing. The liquid hand disinfectant formulation is situated at the base-section 125 such as to provide stability to the dispensing system 100 when placed on a floor. The mid-section 120 of the housing encloses a drain reservoir chassis 165 that can be coupled to the housing and support the drain reservoir 150. Also, it can be seen in FIG. 3 is a pump assembly 170 that is also coupled to the drain reservoir chassis 165 and the mid-section 120 of the housing 110. A fluid conduit 175 can be seen extending from the pump assembly 170 into the liquid hand disinfectant supply 160. The fluid conduit 175 can be of a length that can reach up to the bottom of the reservoir 160 such as to draw the liquid disinfectant preparation in the reservoir. The pump assembly 170 can be electrically operated to draw liquid disinfectant preparation/formulation from liquid hand disinfectant supply 160 through the fluid conduit 175. Another fluid conduit 180 can be seen extended upwards from the pump assembly 170. The fluid conduit 180 can connect to the spout 130 for delivering the liquid hand disinfectant formulation from the liquid hand disinfectant supply to the spout for dispensing.

Figure 4:
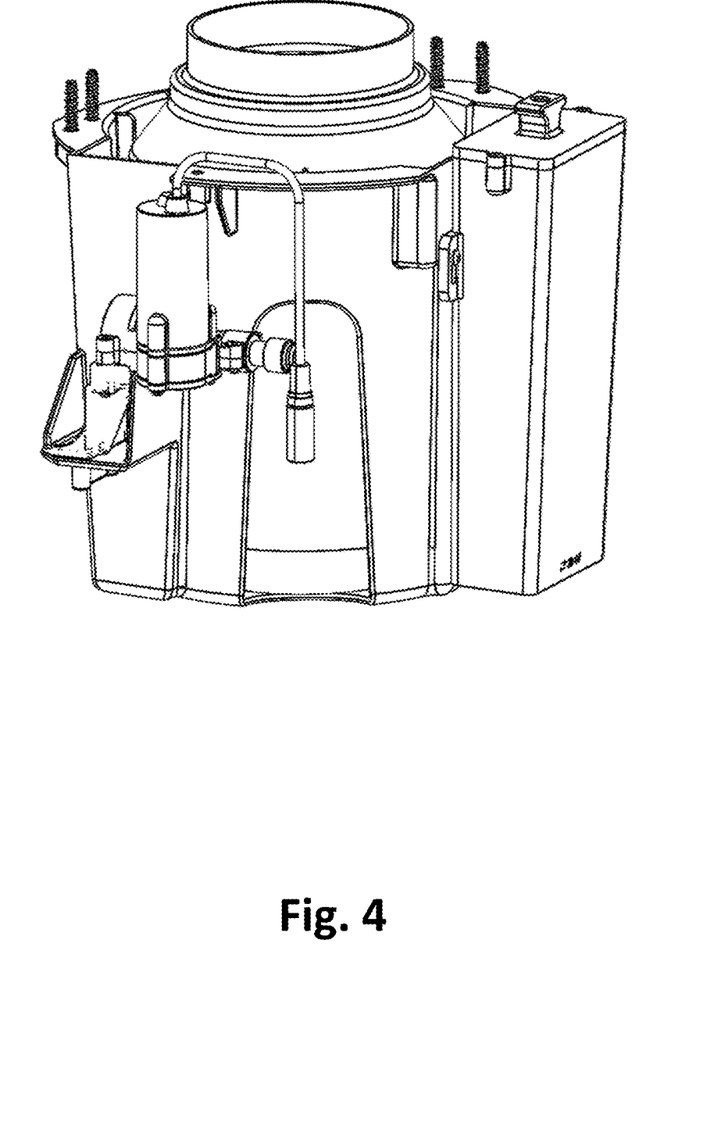
FIG. 4 shows the drain reservoir chassis which supports the drain reservoir, pump assembly, and the battery compartment according to an exemplary embodiment of the present invention.
Figure 5:
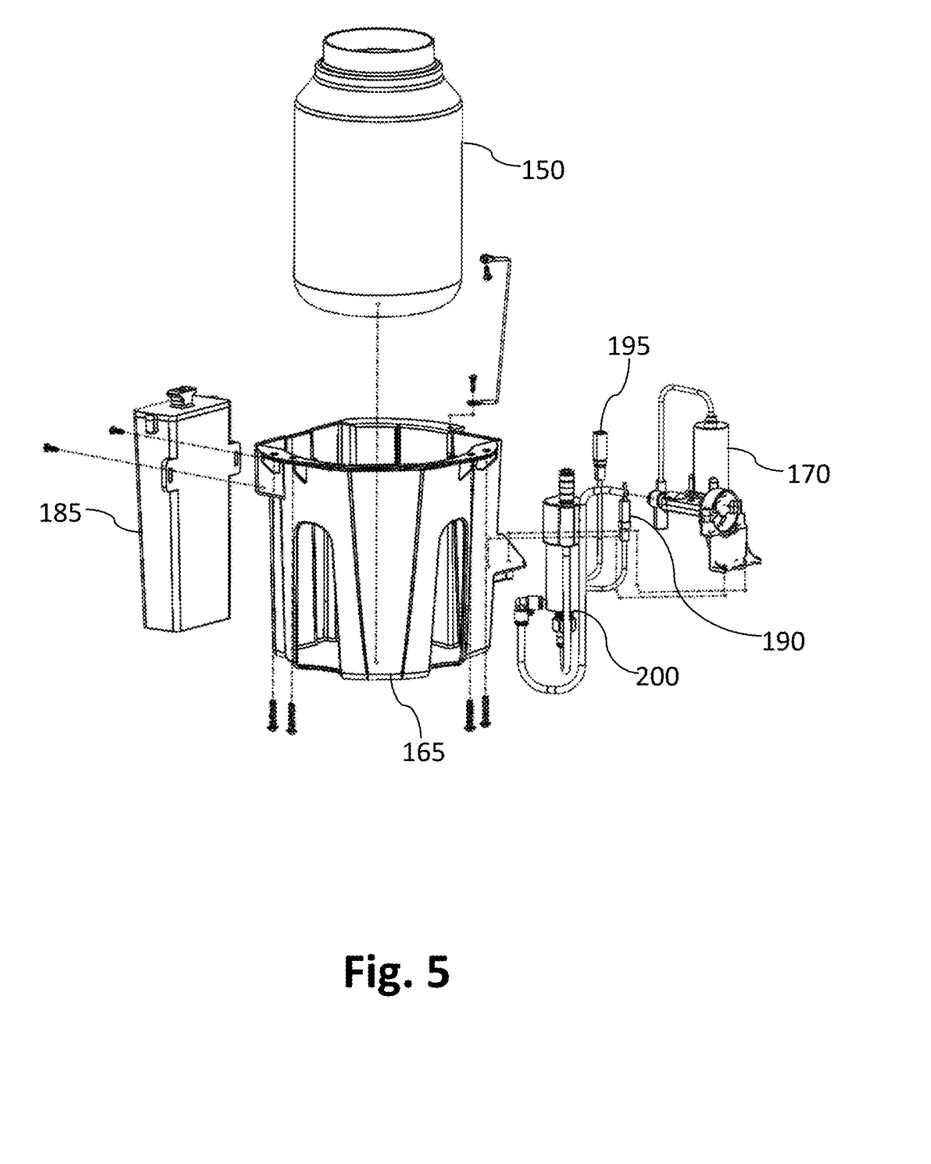
FIG. 5 is an exploded view of the drain reservoir chassis, drain reservoir, pump assembly, and the battery compartment shown in FIG. 4, and the air compressor, according to an exemplary embodiment of the present invention.
Figure 6:
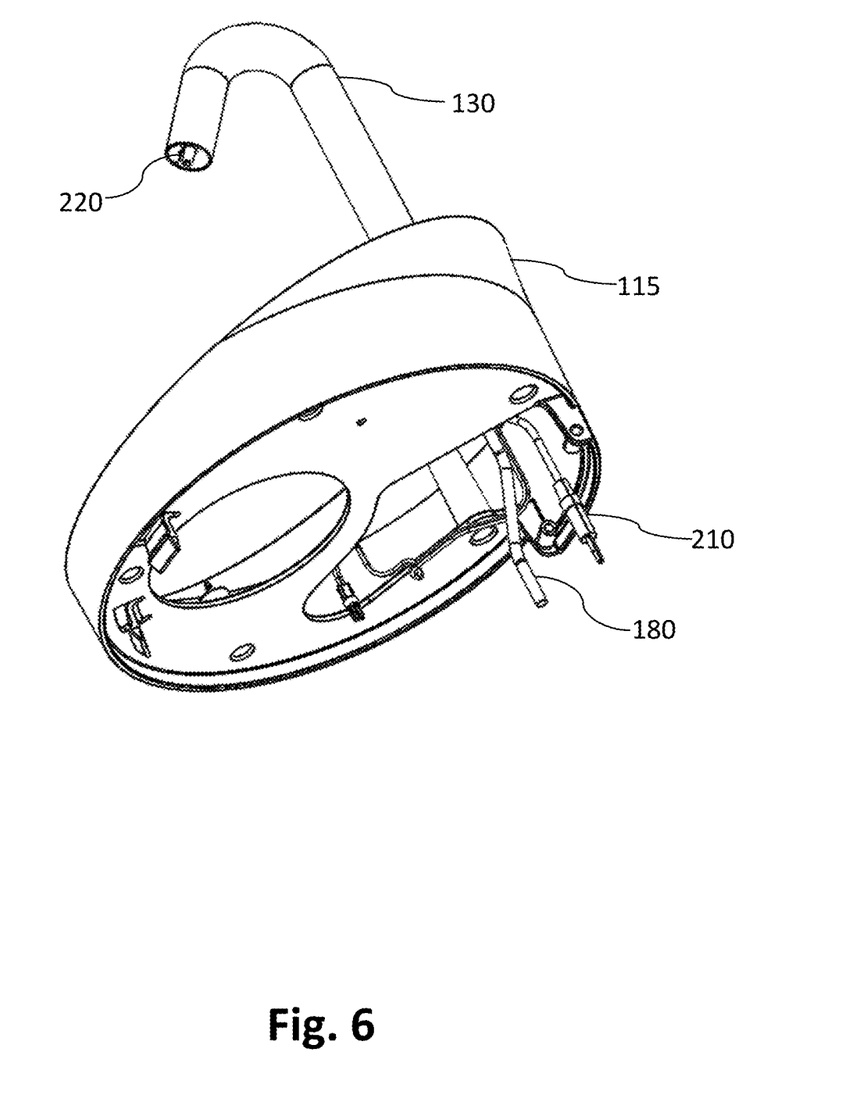
FIG. 6 is a bottom perspective view of the top section of the liquid hand disinfectant dispensing station, according to an exemplary embodiment of the present invention.

FIG. 4 shows the inner components of the mid-section of the housing 110 and FIG. 5 shows an exploded view of the same for clarity and understanding. FIG. 5 shows the drain reservoir chassis 165, the drain reservoir 150, the pump assembly 170, a battery unit 185, a sensor cable 195, and the power cable 190. Also, it can be seen in FIG. 5 is the air compressor 200 that is connected to the pump assembly 170. The air compressor can be used for dispensing a foam liquid hand disinfectant formulation. This can help in uniformly spread disinfectant formulation over the hands preventing any wastage and efficiently sanitizing the hands. The air can be dispersed with the liquid disinfectant to generate a foaming disinfectant. The battery unit 185 can power the pump assembly, the compressor, and a sensor unit coupled in the spout. More clearly seen in FIG. 6 which is a bottom perspective view of the top section of the housing. It can be seen in FIG. 6 is the fluid conduit 180 extending downwards that can be connected to the pump assembly 170. Additional sensor cable 210 can also be seen that can be connected to the sensor cable 195 through sockets at the ends of two-part sensor cables. The sensor cable connects a sensor on the top of the dispensing station to the pump assembly, such as activation of the sensor can send a signal to the pump assembly, which upon receiving the signal can operate to dispense a predetermined dose of the liquid disinfectant formulation from the reservoir. The sensor can be an infrared sensor or a proximity sensor that can detect the presence of a hand under the nozzle of the spout. FIG. 6 shows an infrared sensor 220 coupled to the nozzle of the spout.

The pump assembly 170 can be a micro-dose fluid pump that can dispense a small dose of liquid disinfectant formulation from a large volume reservoir. The micro-dose liquid pump can be electrically driven, wherein the power can be supplied by the power unit 155 and the battery 185. It is to be understood that the pump assembly 170 can be powered from any other power source, without departing from the scope of the present invention. Alternatively, the pump assembly 170 can also be manually operated. In one case, a foot-operated actuator can extend from the base-section of the housing, which can be actuated to dispense a single dose of the liquid disinfectant formulation. Instead of the foot pedal, a hand-actuated lever can also be provided for manual pumps. Also, in the electrically operated pump assembly, the sensor can be replaced by a button, wherein the actuation of the button turns on the power supply to the pump assembly. The micro-dose pump can be configured to dispense a dose of liquid disinfectant formulation that can be of 0.5 mL to 2.0 mL volume.

The top-section and the mid-section of the dispensing station can couple through a hinge joint. This allows the top section to easily lift-up gaining access to the middle section. Upon lifting the top section, the drain reservoir can be removed, emptied, and returned into the drain reservoir chassis. The platform 135 of the top section 115, also described above, can have a slope to channel excess or dripped disinfectant formulation into a drain aperture 145. Valley 140 can also have a beveled edge that can further facilitate the liquid disinfectant to flow down into the drain aperture and into the drain reservoir. Also, periphery 150 of platform 135 can have an upstanding slope that prevents the liquid disinfectant from dripping on the floor but facilitate channeling the liquid disinfectant into the valley and into the drain aperture. This is important because the liquid disinfectant if dripped on the floor can cause slip/fall hazard. The periphery 150 can resemble a sloped lip interior edge around the sloped platform 135 which keeps excess liquid disinfectant from dripping over the top-section and onto the floor surrounding the dispensing station. This is a critical feature of the dispensing station, as a user may need enough space to evenly rub the disinfectant on their hands, and there is a likelihood the excess liquid disinfectant may drip from the hands over the platform and the surrounding lip. The design of the platform and the surrounding lip facilitate the dripped disinfectant liquid to channel into the valley and the drain aperture. Additionally, the size of the freestanding dispensing station is broad, and so the dimension of the top section, which provides enough area for rubbing the hands with the liquid disinfectant and to collect the dripped liquid disinfectant from the rubbing hands. Moreover, the sloped lip interior edge 150 and the sloped platform 135 as shown in FIG. 1 can prevent rushing water from entering the drain aperture but cause the water to run-off the top-section 115. During heavy rains when used in exterior environments, the slope of the lip interior edge 150 and the platform 135 can allow the rainwater to quickly flow down the platform 135 and flow over the lip interior edge 150. The design of the sloped platform and its upstanding surrounding sloped lip can prevent the water from entering the drain aperture but run-off the top section.

Additionally, the drain aperture 145 can be positioned over the opening of the drain reservoir 150. This prevents the need for any conduit and tubing to direct the flow of liquid into the drain reservoir. It is known to a skilled person that the tubing can be clogged by the collected debris especially when the dispensing station is placed in exterior locations. The disclosed design of the valley and the drain aperture do not require the tubing and prevent the clogging of passage, thus prevent any chances of the liquid being collected on the top of the dispensing station.

Figure 7:
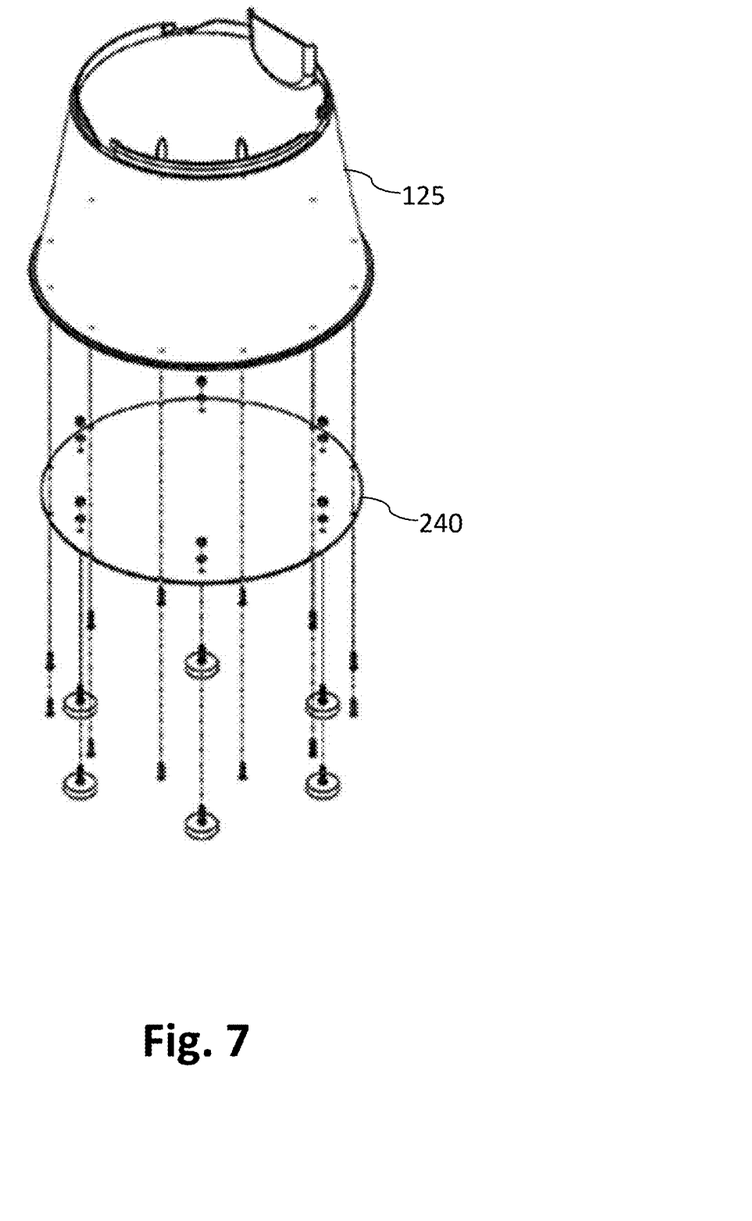
FIG. 7 is an exploded view of the base section of the liquid hand disinfectant dispensing station, according to an exemplary embodiment of the present invention.

Referring to FIG. 7, which shows an exploded view of the base-section having a plate 240 that covers the bottom of the hollow base section. The base plate 240 can have gaps or passage that allows a liquid to escape. In case, the liquid disinfectant in the drain reservoir overflow may be due to neglect, the liquid can overflow into the drain reservoir chassis. The chassis 165, as shown in FIG. 5, can have cutout sections at the bottom edges through which the liquid can flow down into the base section. The liquid can then escape out the base-section through the gap. This prevents the liquid dispenser from filling-up by the overflowing liquid disinfectant from the drain reservoir, which may otherwise harm the components, such as battery and pump assembly.

The disclosed dispensing station can be constructed of materials suitable for both indoor and outdoor use including plastics formed through injection molding in whole or in part, stainless steel in whole or in part, and other materials suitable for constructing a variety of sizes dependent on the number of dispenser spouts, liquid volume requirements, mobility requirements, and aesthetic requirements as may be required by the user. In one exemplary embodiment, the dispensing station can be of a height ranging between 30" inches and 40" inches not including dispensing spout. The spout can be 5-12 inches in height. An adult of an average height can easily access the spout without bending. The size of the dispensing station can vary based on the volume capacity of the liquid hand disinfectant reservoir size requirement. Both the diameter and the height of the dispensing station can be changed depending on the desired capacity of the dispensing station. The dispensing station can be set flush on a floor or ground.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above-described embodiment, method, and examples, but by all embodiments and methods within the scope and spirit of the invention as claimed.

What is claimed is:

1. A freestanding liquid hand disinfectant dispensing station comprising:
   an upstanding housing having a base-section, a mid-section above the base-section, and a top-section above the mid-section, wherein the base-section, the mid-section, and the top-section separate from each other;
   the base-section is hollow and contains a source of liquid hand disinfectant formulation, wherein the base-section is of a size to contain the liquid hand disinfectant formulation in a volume capacity ranging from 2 liters to 100 liters;
   a pump assembly mounted in the mid-section, the pump assembly in fluid communication with the liquid hand disinfectant formulation and a spout, wherein the pump assembly is configured to draw the liquid hand disinfectant formulation and dispense a predetermined amount of the liquid hand disinfectant formulation through the spout;
   the spout mounted on a top surface of the top-section, the top surface having a proximal end and a distal end, the spout is mounted on the proximal end of the top surface, the top surface is sloped downwards from the proximal end towards the distal end, the distal end of the top surface having a valley with a drain aperture at bottom of the valley;
   wherein the dispensing station further comprises a chassis coupled to an inner surface of the mid-section of the housing; and
   a drain reservoir removably mounted in the chassis, the drain reservoir having an opening which is in fluid communication with the drain aperture.

2. The dispensing station according to claim 1, wherein the predetermined amount of the liquid hand disinfectant formulation is in the range of 0.5 to 2.0 ml.

3. The dispensing station according to claim 1, wherein the dispensing station further comprises an air compressor in fluid communication with the pump assembly, wherein the air compressor is configured to disperse air in the liquid hand disinfectant formulation resulting in the dispensing of foam liquid hand disinfectant formulation from the spout.

4. The dispensing station according to claim 3, wherein the dispensing station further comprises a battery to power the pump assembly and the air compressor.

5. The dispensing station according to claim 3, wherein the dispensing station further comprises a sensor configured to detect a presence of a hand below a nozzle of the spout, the sensor operably coupled to the pump assembly.

6. The dispensing station of claim 1, wherein the top-section is configured to be opened for removing the drain reservoir.

7. The dispensing station of claim 1, wherein the mid-section is configured to be removed for gaining access to install, remove, or replace the liquid hand disinfectant formulation.

8. The dispensing station of claim 1, wherein the housing is frustoconical in shape having a diameter of a bottom of the base-section about 28 to 45% larger than a diameter of the top of the top-section for enhanced stability.

9. The dispensing station of claim 1, wherein the top surface of the top-section includes a sloped platform and an upstanding sloped lip around the periphery of the platform, the platform and the lip are configured to channel any dripped liquid hand disinfectant formulation into the valley.

10. The dispensing station of claim 1, wherein the top-section and the middle-section are coupled through a hinge joint, wherein the top-section can be opened providing access to a interior chassis, power unit, battery compartment, pump assembly, air compressor, sensor cable and power cable.

11. The dispensing station of claim 9, wherein the platform and the lip are configured to permit a small amount of liquid to flow into the drain aperture but not rushing water, wherein the rushing water runs off the lip of the top surface.

12. The dispensing station of claim 11, wherein the rushing water is from rain when used in exterior environments.

13. The dispensing station of claim 4, wherein the base-section comprises a hollow housing and a base plate covering a bottom of the hollow housing, the base plate having gaps to permit liquid to escape.

14. The dispensing station of claim 13, wherein the chassis comprises cutouts in a bottom edge for the liquid to escape into the base-section.

15. The dispensing station of claim 4, wherein the drain aperture is positioned above the opening of the drain reservoir and the drain aperture does not having any tubing.

16. The dispensing station of claim 1, wherein the top surface is of a dimension at least to facilitate rubbing the liquid hand disinfectant over a users hands while any excesses of the liquid hand disinfectant from the hands drips onto the top surface.

17. The dispensing station of claim 1, wherein the valley comprises a beveled edge.

* * * * *